United States Patent
Heil et al.

(10) Patent No.: US 9,802,895 B2
(45) Date of Patent: Oct. 31, 2017

(54) INDOLE AND BENZIMIDAZOLECARBOXAMIDES AS INSECTICIDES AND ACARICIDES

(71) Applicant: BAYER CROPSCIENCE AKTIENGESELLSCHAFT, Monheim am Rhein (DE)

(72) Inventors: Markus Heil, Leichlingen (DE); Eike Kevin Heilmann, Duesseldorf (DE); Werner Hallenbach, Monheim (DE); Kerstin Ilg, Cologne (DE); Ulrich Goergens, Ratingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/119,046

(22) PCT Filed: Feb. 13, 2015

(86) PCT No.: PCT/EP2015/053065
§ 371 (c)(1),
(2) Date: Aug. 15, 2016

(87) PCT Pub. No.: WO2015/121406
PCT Pub. Date: Aug. 20, 2015

(65) Prior Publication Data
US 2016/0355476 A1    Dec. 8, 2016

(30) Foreign Application Priority Data
Feb. 17, 2014  (EP) .................... 14155320

(51) Int. Cl.
C07D 209/42 (2006.01)
C07D 235/24 (2006.01)
A01N 53/00 (2006.01)

(52) U.S. Cl.
CPC ........... C07D 209/42 (2013.01); A01N 53/00 (2013.01); C07D 235/24 (2013.01)

(58) Field of Classification Search
CPC ..... C07D 209/42; C07D 235/24; A01N 53/00
See application file for complete search history.

(56) References Cited

U.S. PATENT DOCUMENTS

| 8,710,242 B2 | 4/2014 | Heil et al. |
| 8,889,878 B2 | 11/2014 | Heil et al. |
| 9,107,411 B2 * | 8/2015 | Heil ............... A01N 43/38 |
| 9,345,247 B2 | 5/2016 | Heil et al. |
| 2006/0183753 A1 | 8/2006 | Erguden et al. |
| 2009/0041722 A1 | 2/2009 | Liu et al. |

FOREIGN PATENT DOCUMENTS

| EP | 1460064 A1 | 9/2004 | |
| WO | 2004/032921 A1 | 4/2004 | |
| WO | 2004/056768 A2 | 7/2004 | |
| WO | 2007/115938 A1 | 10/2007 | |
| WO | 2010032622 A1 | 3/2010 | |
| WO | 2010/054138 A2 | 5/2010 | |
| WO | 2010/126164 A1 | 11/2010 | |
| WO | 2012/119984 A1 | 9/2012 | |
| WO | WO2012119984 A1 * | 9/2012 | ............. A01N 43/38 |
| WO | 2014/026984 A1 | 2/2014 | |
| WO | 2015/107133 A1 | 7/2015 | |

OTHER PUBLICATIONS

International Search Report dated May 8, 2015, in counterpart application No. PCT/EP2015/053065.
European Search Report dated Jul. 24, 2014, issued in counterpart European Application No. 14155320.

* cited by examiner

*Primary Examiner* — Yong Chu
(74) *Attorney, Agent, or Firm* — McBee Moore Woodward & Vanik IP, LLC; Susan McBee; David Woodward

(57) ABSTRACT

The present invention relates to compounds of the general formula (I),

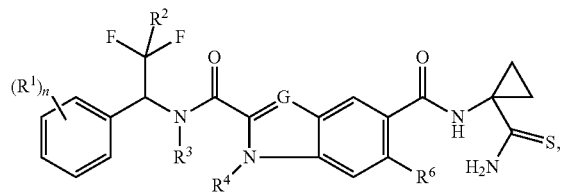

in which $R^1$ to $R^6$, G and n have the meanings given in the description and to a process for their preparation and to their use as insecticides and acaricides.

15 Claims, No Drawings

INDOLE AND BENZIMIDAZOLECARBOXAMIDES AS INSECTICIDES AND ACARICIDES

CROSS REFERENCE TO RELATED APPLICATIONS

This application is a §371 National Stage Application of PCT/EP2015/053065, filed 13 Feb. 2015, which claims priority to EP 14155320.6, filed 17 Feb. 2014.

BACKGROUND

Field of the Invention

The present invention relates to novel pesticides, to a process for preparation thereof and to the use thereof as active compounds, especially to the use thereof as insecticides and acaricides.

Description of Related Art

Indole-2-carboxamides and benzimidazole-2-carboxamides and their use as medicaments have been described in the literature, see, for example, WO-A-2010/126164, WO-A-2010/054138, US 2009/0041722, WO-A-2007/115938, EP1460064, WO-A-2004-A-056768, WO-A-2004/032921, WO-A-20010/32622. WO-A-2012/119984 discloses indole-2-carboxamides and benzimidazole-2-carboxamides and their use as crop protection agents. In this publication, Example 273 discloses a compound having an aminothiocarbonylcyclopropyl substitution of the amide radical at the six-membered indole ring. However, at the phenyl ring this compound is only monosubstituted by trifluoromethyl.

SUMMARY

It has now been found, surprisingly, that certain novel indole- and benzimidazolecarboxamides have strong insecticidal and acaricidal properties and are at the same time well tolerated by plants, have favourable homeotherm toxicity and good environmental compatibility. The novel compounds according to the invention have not been disclosed to date.

Modern crop protection compositions have to meet many demands, for example in relation to efficacy, persistence and spectrum of their action and possible use. Questions of toxicity and of combinability with other active compounds or formulation auxiliaries play a role, as does the question of the expense that the synthesis of an active compound requires. In addition, resistances can occur. For all these reasons, the search for novel crop protection agents can never be considered to be complete, and there is a constant need for novel compounds having properties improved over the known compounds at least in relation to individual aspects.

It was an object of the present invention to provide compounds which widen the spectrum of the pesticides under various aspects and/or improve their activity.

The novel compounds of the formula (I) are distinguished in particular by having an aminothiocarbonylcyclopropyl substitution of the amide radical at the six-membered indole ring, and by the phenyl ring being polysubstituted, with at least one of these substituents being halogen. Surprisingly, the combination of these features leads to an improved biological efficacy. This is demonstrated in the biological use examples shown.

The present invention therefore provides compounds of the general formula (I)

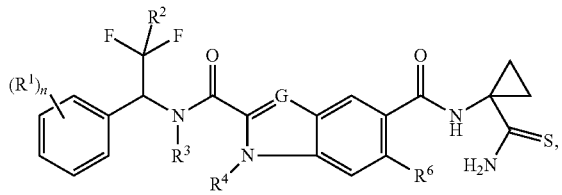

where
R$^1$ represents cyano, fluorine, chlorine, bromine, iodine, difluoromethyl, dichlorofluoromethyl, chlorodifluoromethyl, trifluoromethyl, pentafluoroethyl, chlorotetrafluoroethyl, difluoromethoxy, trifluoromethoxy,
  where at least one substituent R$^1$ represents fluorine, chlorine, bromine or iodine,
R$^2$ represents fluorine, trifluoromethyl or hydrogen,
n represents 2, 3, 4 or 5,
R$^3$ represents hydrogen,
R$^4$ represents hydrogen, methyl, ethyl, prop-1-yl, prop-2-en-1-yl, prop-2-yn-1-yl, ethenyl, but-2-yn-1-yl,
G represents CH or N,
R$^6$ represents cyano, fluorine, chlorine, bromine, methyl, ethyl, difluoromethyl or trifluoromethyl, and also salts and N-oxides of compounds of the formula (I) and their use for controlling animal pests.

DETAILED DESCRIPTION OF A PREFERRED EMBODIMENT

In a preferred embodiment (2-1) of the invention,
R$^1$ represents fluorine, chlorine, bromine, iodine or trifluoromethyl,
  where at least one substituent R$^1$ represents fluorine, chlorine, bromine or iodine,
R$^2$ represents fluorine or hydrogen,
n represents 2, 3 or 4,
R$^3$ represents hydrogen,
R$^4$ represents hydrogen, methyl, ethyl or prop-2-yn-1-yl,
G represents CH or N,
R$^6$ represents chlorine, bromine, methyl or trifluoromethyl, and also salts and N-oxides of compounds of the formula (I) and their use for controlling animal pests.

In a particularly preferred embodiment (3-1), R$^1$ represents fluorine, chlorine, bromine or trifluoromethyl and n represents 2, 3 or 4, where at least one substituent R$^1$ represents fluorine or chlorine and all other groups, radicals and substituents have the meaning mentioned above for the preferred embodiment (2-1).

In a further particularly preferred embodiment (3-2), R$^6$ represents chlorine or methyl, where all other groups, radicals and substituents have the meaning mentioned above for the preferred embodiment (2-1) or the meaning mentioned above for the particularly preferred embodiment (3-1).

In a further particularly preferred embodiment (3-3), G represents CH, where all other groups, radicals and substituents have the meaning mentioned above for the preferred embodiment (2-1) or the meaning mentioned above for the particularly preferred embodiment (3-1) or the meaning mentioned above for the particularly preferred embodiment (3-2).

In a further particularly preferred embodiment (3-4), G represents N, where all other groups, radicals and substituents have the meaning mentioned above for the preferred embodiment (2-1) or the meaning mentioned above for the particularly preferred embodiment (3-1) or the meaning mentioned above for the particularly preferred embodiment (3-2).

According to the invention, the compounds of the formula (I) can be substituted by identical or different substituents $R^1$.

If appropriate, the compounds of the formula (I) may be present in various polymorphic forms or as a mixture of various polymorphic forms. Both the pure polymorphs and the polymorph mixtures form part of the subject-matter of the invention and can be used in accordance with the invention.

The compounds of the formula (I) include any E/Z isomers and diastereomers or enantiomers which exist.

The substituted indole- and benzimidazolecarboxamides are defined in general terms by the formula (I). Preferred radical definitions for the formulae specified above and hereinafter are given below. These definitions apply to the end products of the formula (I) and likewise to all intermediates.

The particular number of substituents n in the formula (I) includes only the substituents other than hydrogen. For this reason, hydrogen is also not included in the definition of $R^1$. Of course, hydrogen is always present as a substituent when no $R^1$ substituent is present at the site in question.

In the preferred definitions, unless stated otherwise, halogen is selected from the group of fluorine, chlorine, bromine and iodine, preferably in turn from the group of fluorine, chlorine and bromine In the particularly preferred definitions, unless stated otherwise, halogen is selected from the group of fluorine, chlorine, bromine and iodine, preferably in turn from the group of fluorine, chlorine and bromine.

Halogen-substituted radicals, for example haloalkyl, are mono- or polyhalogenated up to the maximum possible number of substituents. In the case of polyhalogenation, the halogen atoms can be identical or different. In this case, halogen is fluorine, chlorine, bromine or iodine, especially fluorine, chlorine or bromine.

Saturated or unsaturated hydrocarbyl radicals such as alkyl, alkenyl or alkynyl may each be straight-chain or branched to the extent possible, including in combination with heteroatoms, as, for example, in alkoxy.

Optionally substituted radicals may be mono- or polysubstituted, where the substituents in the case of polysubstitution may be the same or different.

The radical definitions or elucidations given above in general terms or within areas of preference apply to the end products and correspondingly to the starting materials and intermediates. These radical definitions can be combined with one another as desired, i.e. including combinations between the respective preferred ranges.

Preference is given in accordance with the invention to compounds of the formula (I) in which a combination of the meanings listed above as preferred is present.

Particular preference is given in accordance with the invention to compounds of the formula (I) in which a combination of the meanings listed above as particularly preferred is present.

Compounds according to the invention which are likewise preferred are the compounds of the general formula (I) shown in Table 1.

The present compounds of the general formula (I) may optionally have a chiral carbon atom.

According to the rules of Calm, Ingold and Prelog (CIP rules), these substituents may have either an (R) configuration or an (S) configuration.

The present invention encompasses compounds of the general formula (I) both with (S) and with (R) configuration at the particular chiral carbon atoms, i.e. the present invention encompasses the compounds of the general formula (I) in which the carbon atoms in question each independently have
 (1) an (R) configuration; or
 (2) an (S) configuration.
aufweisen. When more than one chiral centre is present in the compounds of the general formula (I), any desired combinations of the configurations of the chiral centres are possible, which means that
 (1) one chiral centre may have (R) configuration and the other chiral centre (S) configuration;
 (2) one chiral centre may have (R) configuration and the other chiral centre (R) configuration; and
 (3) one chiral centre may have (S) configuration and the other chiral centre (S) configuration.

The compounds of the formula (I) likewise encompass any diastereomers or enantiomers and E/Z isomers which exist, and also salts and N-oxides of compounds of the formula (I), and the use thereof for control of animal pests.

The invention also relates to the use of the compounds of the general formula (I) according to the invention for production of pesticides.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any desired mixtures of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always comprises the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are effective against normally sensitive and resistant species and against all or some stages of development. The abovementioned pests include:

pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici*;

from the class of the Chilopoda, for example *Geophilus* spp., *Scutigera* spp.;

from the order or the class of the Collembola, for example *Onychiurus armatus; Sminthurus viridis*;

from the class of the Diplopoda, for example *Blaniulus guttulatus*;

from the class of the Insecta, for example from the order of the Blattodea, for example *Blatta orientalis, Blattella asahinai, Blattella germanica, Leucophaea maderae, Panchlora* spp., *Parcoblatta* spp., *Periplaneta* spp., for example *Periplaneta americana, Periplaneta australasiae, Supella longipalpa*;

from the order of the Coleoptera, for example *Acalymma vittatum, Acanthoscelides obtectus, Adoretus* spp., *Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera, Diabrotica virgifera zeae, Dichocrocis* spp., *Dicladispa armigera, Diloboderus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides*;

from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Fannia* spp., *Gasterophilus* spp., *Glossina* spp., *Haematopota* spp., *Hydrellia* spp.,

*Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex;* from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Nephotettix* spp., for example *Nephotettix cincticeps, Nephotettix nigropictus, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Monalonion atratum, Nezara* spp., for example *Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Diprion* spp., for example *Diprion similis, Hoplocampa* spp., for example *Hoplocampa cookei, Hoplocampa testudinea, Lasius* spp., *Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Microtermes obesi, Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Heliothrips* spp., *Hercinothrips femoralis, Rhipiphorothrips cruentatus, Scirtothrips* spp., *Taeniothrips cardamomi, Thrips* spp., for example *Thrips palmi, Thrips tabaci;* from the order of the Zygentoma (=*Thysanura*), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, for example from the class of the Bivalvia, for example *Dreissena* spp., and also from the class of the Gastropoda, for example *Anion* spp., for example *Anion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp, *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp, *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, especially *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides*

*onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paraphelenchus* spp., *Paratrichodorus* spp., for example *Paratrichodorus minor, Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example *Tylenchorhynchus annulatus, Tylenchulus* spp., for example *Tylenchulus semipenetrans, Xiphinema* spp., for example *Xiphinema index.*

In addition, it is possible to control, from the sub-kingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (mycoplasma-like organisms) and RLO (rickettsia-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be such substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, such as xylene, toluene or alkylnaphthalenes, aromatic or aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkyl sulphonates, alkyl sulphates, arylsulphonates, protein hydrolyzates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids. Further possible auxiliaries are mineral and vegetable oils.

Optionally, yet further auxiliaries may be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and thereby increase the mobility of active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), with particular preference, between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellants and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case. Examples of useful mixing components are the following compounds:

Insecticides /Acaricides/Nematicides:

The active compounds identified here by their common names are known and are described, for example, in the pesticide handbook ("The Pesticide Manual" 16th Ed., British Crop Protection Council 2012) or can be found on the Internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulphan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulphoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulphotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulphan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, taufluvalinate, halfenprox, imiprothrin, kadethrin, permethrin, phenothrin [(1R)-trans isomer], prallethrin, pyrethrins (pyrethrum), resmethrin, silafluofen, tefluthrin, tetramethrin, tetramethrin [(1R) isomers)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulphoxaflor.

(5) Allosteric activators of the nicotinergic acetylcholine receptor (nAChR), for example spinosyns, e.g. spinetoram and spinosad.

(6) Chloride channel activators, for example, avermectins/milbemycins, e.g. abamectin, emamectin benzoate, lepimectin and milbemectin.

(7) Juvenile hormone imitators, for example, juvenile hormone analogues e.g. hydroprene, kinoprene and methoprene or fenoxycarb or pyriproxyfen.

(8) Active compounds with unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulphluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (in particular for Diptera, i.e. dipterans) such as, for example, cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide, further active compounds, for example afidopyropen, azadirachtin, benclothiaz, benzoximate, bifenazate, bromopropylate, chinomethionat, cryolite, dicofol, diflovidazin, fluensulphone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; and also preparations based on *Bacillus firmus* (I -1582, BioNeem, Votivo), and also the following compounds: 3-bromo-N-{2-bromo-4-chloro-6-[(1-cyclopropylethyp)carbamoyl] phenyl}-1-(3-chloropyridin-2-yl)-1H-pyrazole-5-carboxamide (known from WO2005/077934) and 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl] piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl)sulphonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), 4-[5-(3,5-dichlorophenyl)-5-(trifluoromethy)-4,5-dihydro-1,2-oxazol-3-yl]-2-methyl-N-(1-oxidothietan-3-yl)benzamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides

The active compounds specified herein by their common name are known and described, for example, in "Pesticide Manual" or on the Internet (for example: http://www.alanwood.net/pesticides).

(1) Ergosterol biosynthesis inhibitors, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors), for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro- 1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid (3) Respiration inhibitors (respiratory chain inhibitors) that act on complex III of the respiratory chain, for example (3.1) ametoctradin, (3.2) amisulbrom, (3.3) azoxystrobin, (3.4) cyazofamid, (3.5) coumethoxystrobin, (3.6) coumoxystrobin, (3.5) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-[6-(3-chloro-2-methylphenoxy)-5-fluoropyrimidin-4-yl]oxylphenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy}imino)methyl]phenyl}ethanamide, (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide, (4) inhibitors of mitosis and cell division, for example (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity such as, for example, (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copperoxine, (5.28) propamidine, (5.29) propineb, (5.30) sulphur and sulphur preparations such as, for example calcium polysulphide, (5.31) thiram, (5.32) tolylfluanid, (5.33) zineb, (5.34) ziram and (5.35) anilazine.

(6) Resistance inducers, for example (6.1) acibenzolar-S-methyl, (6.2) isotianil, (6.3) probenazole, (6.4) tiadinil and (6.5) laminarin (7) Amino acid and protein biosynthesis inhibitors, for example (7.1), (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors, for example (8.1) fentin acetate, (8.2) fentin chloride, (8.3) fentin hydroxide and (8.4) silthiofam.

(9) Cell wall synthesis inhibitors, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Lipid and membrane synthesis inhibitors, for example (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluoroethyl {3-methyl-1-[(4-methylbenzoyl)amino]butan-2-yl}carbamate.

(12) Nucleic acid synthesis inhibitors, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors, for example (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers, for example (14.1) binapacryl, (14.2) dinocap, (14.3) ferimzone, (14.4) fluazinam and (14.5) mepyldinocap.

(15) Further compounds, for example (15.1) benthiazole, (15.2) bethoxazine, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulphamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20) flumetover, (15.21) fluorimid, (15.22) flusulphamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulphocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3- yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole -1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulphonohydrazide, (15.74) 5-fluoro-2-[(4-fluorobenzypoxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-y;)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-ypoxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl) (phenyl)methylene]amino}oxy)methyl]pyridin-2-yl}carbamate, (15.91) phenazine-1-carboxylic acid, (15.92) quinolin-8-ol, (15.93) quinolin-8-ol sulphate (2:1), (15.94) tert-butyl {6[({[1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-y;)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl] nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl] nicotinamide, (15.115) (5-bromo-2-methoxy-4-methylpyridin-3-yl)(2,3,4-trimethoxy-6-methylphenyl) methanone, (15.116) N-[2-(4-{[3-(4-chlorophenyl)prop-2-yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene] amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl] (pyridin-3-yl)methanol, (15.125) (S)-[3-(4-chloro-2-fluorophenyl)-5-(2,4-difluorophenyl)-1,2-oxazol-4-yl] (pyridin-3-yl)methanol, (15.126) (R)-[3-(4-chloro-2-fluorophenyl)-5-(2,4-difluorophenyl)-1,2-oxazol-4-yl] (pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulphanyl)-1-{[3-(2-chlorophenyl)-2-(2,4-difluorophenypoxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenypoxiran-2-yl]methyl}-2,4-dihydro-3H-1,2,4-triazole-3-thione, (15.132) 2-{[rel(2R,3R)-3-(2-chlorophenyl)-2-(2,4-difluorophenypoxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran- 2-yl]methyl}-1H-1,2,4-triazol-5-yl thiocyanate, (15.134) 1-{[rel(2R,3R)-3-(2-chlorophenyl)-2-(2,4-difluorophenypoxiran-2-yl]methyl}-1H-1,2,4-triazol-5-yl thiocyanate, (15.135) 5-(allylsulphanyl)-1-{[rel(2R,3S)-3-(2-chlorophenyl)-2-(2,4-difluorophenypoxiran-2-yl]methyl}-1H-1,2,4-triazole, (15.136) 5-(allylsulphanyl)-1-{[rel(2R,3R)-3-(2-chlorophenyl)-2-(2,4-difluorophenypoxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy -2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl) quinazoline, (15.147) 24643-fluoro-4-methoxy phenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole -4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole -4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethypbenzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazole-5-amine. All the mixing components mentioned in classes (1) to (15), as the case may be, may form salts with suitable bases or acids if they are capable of doing so on the basis of their functional groups.

Biological Pesticides as Mixing Components

The compounds of the formula (I) can be combined with biological pesticides. Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, in particular *B. cereus* strain CNCM I-1562 or *Bacillus firmus*, strain I-1582 (Accession number CNCM I-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), or *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. *kurstaki* strain HD-1, or *B.*

*thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Acession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (now: *Isaria fumosorosea*), in particular strain IFPC 200613, or strain Apopka 97 (Accesion No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39. (Accession Number CNCM I-952).

Examples of viruses which are used or can be used as biological pesticides are:

*Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora* monosporum, *Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Sullins* spp., *Streptomyces* spp.

Examples of plant extracts and products formed by microorganisms, including proteins and secondary metabolites, which are used or can be used as biological pesticides are:

Allium sativum, Artemisia absinthium, azadirachtin, Biokeeper WP, Cassia nigricans, Celastrus angulatus, Chenopodium anthelminticum, chitin, Armour-Zen, Dryopteris filixmas, Equisetum arvense, Fortune Aza, Fungastop, Heads Up (Chenopodium quinoa saponin extract), pyrethrum/pyrethrins, Quassia amara, Quercus, Quillaja, Regalia, "Requiem™ Insecticide", rotenone, ryania/ryanodine, Symphytum officinale, Tanacetum vulgare, thymol, Triact 70, TriCon, Tropaeulum majus, Urtica dioica, Veratrin, Viscum album, Brassicaceae extract, especially oilseed rape powder or mustard powder.

Safeners as Mixing Components

The compounds of the formula (I) can be combined with safeners such as, for example, benoxacor, cloquintocet (-mexyl), cyometrinil, cyprosulphamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4. 5]decane (CAS 71526-07-3), 2,2,5-trimethyl-3-(dichloroacetyl)-1,3-oxazolidine (CAS 52836-31-4).

Plants and Plant Parts

All plants and parts of plants can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapevines).

Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Parts of plants shall be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested material and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are increased resistance of the plants against animal and microbial pests, such as insects, arachnids, nematodes, mites, slugs and snails owing, for example, to toxins formed in the plants, in particular those produced in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. However, the treatment of seed entails a series of problems which cannot always be solved in a satisfactory manner Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of pesticides.

The present invention therefore in particular also relates to a method for the protection of seed and germinating plants, from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It also further comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions or compounds of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beets (for example sugarbeets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis.*

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. Thus, for example, it is possible to use seed which has been harvested, cleaned and dried down to a moisture content which allows storage. Alternatively, it is also possible to use seed which, after drying, has been treated with, for example, water and then dried again, for example priming.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing compounds of the formula (I) with customary additives such as, for example, customary extenders and also solvents or diluents, dyes, wetting agents, dispersants, emulsifiers, antifoams, preservatives, secondary thickeners, adhesives, gibberellins and also water.

Dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are customary for the formulation of active agrochemical compounds. Preference is given to using alkyl naphthalenesulphonates, such as diisopropyl or diisobutyl naphthalenesulphonates.

Suitable dispersants and/or emulsifiers which may be present in the seed dressing formulations usable in accordance with the invention are all nonionic, anionic and cationic dispersants customary for the formulation of active agrochemical compounds. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances customary for the formulation of active agrochemical compounds. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions. Preferred examples include cellulose derivatives, acrylic acid derivatives, xanthan, modified clays and finely divided silica.

Useful adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

Gibberellins which may be present in the seed dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmitte", vol. 2, Springer Verlag, 1970, pp. 401-412).

The seed dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom, all mixing units usable customarily for the seed dressing are useful. Specifically, the procedure in seed dressing is to place the seed into a mixer in batchwise or continuous operation, to add the particular desired amount of seed dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the animal health field, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;

from the order of the Heteropterida, for example *Cimex* spp., *Triatoma* spp., *Rhodnius* spp., *Panstrongylus* spp.; and also nuisance and hygiene pests from the order of the Blattarida.

Arthropods further include:

from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus (Boophilus)* spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa Include:

Mastigophora (Flagellata), for example Trypanosomatidae, for example, *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example, *Giardia lamblia*, *G. canis*;

Sarcomastigophora (Rhizopoda) such as Entamoebidae, for example, *Entamoeba histolytica*, Hartmanellidae, for example, *Acanthamoeba* sp., *Harmanella* sp.;

Apicomplexa (Sporozoa) such as Eimeridae, for example, *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E ninakohlyakimovae*, *E. ovis*, *E. parva*, *E. pavonis*, *E. perforans*, *E. phasani*, *E. piriformis*, *E. praecox*, *E. residua*, *E. scabra*, *E. spec.*, *E. stiedai*, *E. suis*, *E. tenella*, *E. truncata*, *E. truttae*, *E. zuernii*, *Globidium* spec., *Isospora belli*, *I. canis*, *I. felis*, *I. ohioensis*, *I. rivolta*, *I.* spec., *I. suis*, *Cystisospora* spec., *Cryptosporidium* spec., in particular *C. parvum*; such as Toxoplasmadidae, for example, *Toxoplasma gondii, Hammondia heydornii, Neospora caninum, Besnoitia besnoitii;* such as Sarcocystidae, for example, *Sarcocystis bovicanis, S. bovihominis, S. ovicanis, S. ovifelis, S. neurona, S.* spec., *S. suihominis,* such as Leucozoidae, for example, *Leucozytozoon simondi,* such as Plasmodiidae, for example, *Plasmodium berghei, P. falciparum, P. malariae, P. ovale, P. vivax, P.* spec., such as Piroplasmea, for example, *Babesia argentina, B. bovis, B. canis, B.* spec., *Theileria parva, Theileria* spec., such as Adeleina, for example, *Hepatozoon canis, H.* spec.

Pathogenic endoparasites, which are helminths, include Platyhelmintha (e.g. Monogenea, cestodes and trematodes), roundworms, Acanthocephala, and Pentastoma. These include:

monogenea: for example: *Gyrodactylus* spp., *Dactylogyrus* spp., *Polystoma* spp.;

cestodes: from the order of the Pseudophyllidea, for example: *Diphyllobothrium* spp., *Spirometra* spp., *Schistocephalus* spp., *Ligula* spp., *Bothridium* spp., *Diplogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

roundworms: Trichinellida, for example *Trichuris* spp., *Capillaria* spp., *Paracapillaria* spp., *Eucoleus* spp., *Trichomosoides* spp., *Trichinella* spp.;

from the order of the Tylenchida, for example: *Micronema* spp., *Strongyloides* spp.;

from the order of the Rhabditida, for example; *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example *Filicollis* spp.; from the order of the Moniliformida, for example: *Moniliformis* spp.;

from the order of the Echinorhynchida, for example, *Acanthocephalus* spp., *Echinorhynchus* spp., *Leptorhynchoides* spp.;

Pentastoma: from the order of the Porocephalida, for example, *Linguatula* spp.

In the veterinary field and in animal keeping, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as medicament.

A further aspect refers to the use of a compound of the formula (I) as an antiendoparasitic agent, in particular as a helminthicidal agent or antiprotozoic agent. Compounds of the formula (I) are suitable for use as an antiendoparasitic agent, especially as a helminthicidal agent or antiprotozoic agent, for example in animal husbandry, in animal breeding, in buildings for live stock and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in buildings for live stock or in the hygiene sector.

Vector Control

The compounds of the formula (I) can also be used in vector control. In the context of the present invention, a vector is an arthropod, especially an insect or arachnid, capable of transmitting pathogens, for example, viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes

Anopheles: malaria, filariasis;

Culex: Japanese encephalitis, filariasis, other viral diseases, transmission of worms;

Aedes: yellow fever, dengue fever, filariasis, other viral diseases;

Simuliidae: transmission of worms, in particular Onchocerca volvulus;

2) Lice: skin infections, epidemic typhus;

3) Fleas: plague, endemic typhus;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), CrimeanCongo haemorrhagic fever, borreliosis;

6) Ticks: borellioses such as Borrelia duttoni, tick-borne encephalitis, Q fever (Coxiella burnetii), babesioses (Babesia canis).

Examples of vectors in the context of the present invention are insects, for example aphids, flies, leafhoppers or thrips, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forestry, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic sector, in the hygiene sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

Description of the Processes and Intermediates

Compounds of the general formula (I)

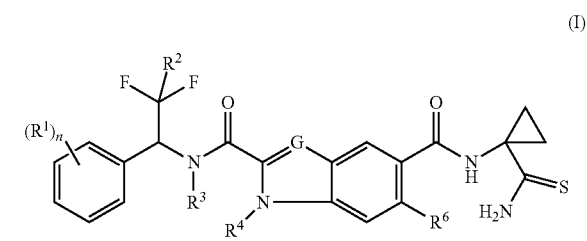

can be obtained by reacting carboxylic acids of the general formula (II)

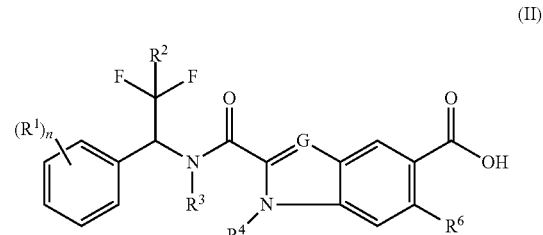

with 1-aminocyclopropanecarbothioamide of the formula (VII)

in the presence of a condensing agent such as, for example, [benztriazol-1-yloxy(dimethylamino)methylene]dimethylammonium hexafluorophosphate.

Some indolecarboxylic acids of the formula (IIa) are known (cf., for example, WO-A-2012/119984). Analogously to the process described in WO-A-2012/119984, it is also possible to obtain novel compounds of the formula (IIa) according to Scheme 1. Here, $L^4$ represents hydrogen.

Scheme 1
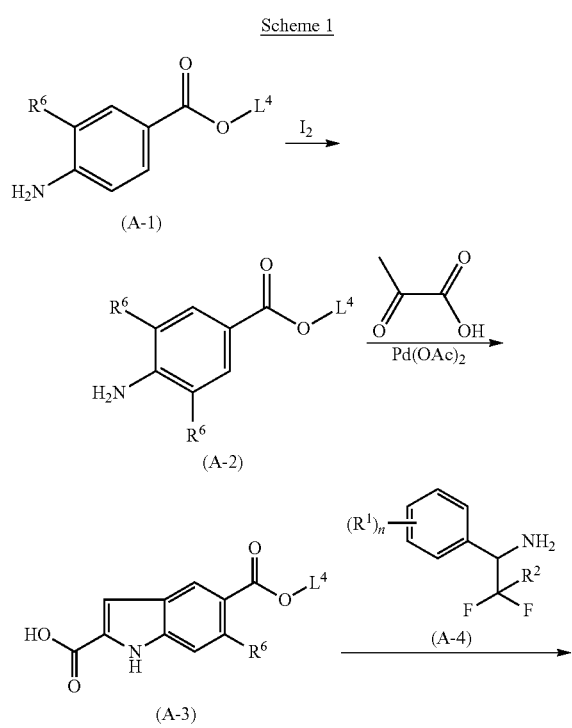
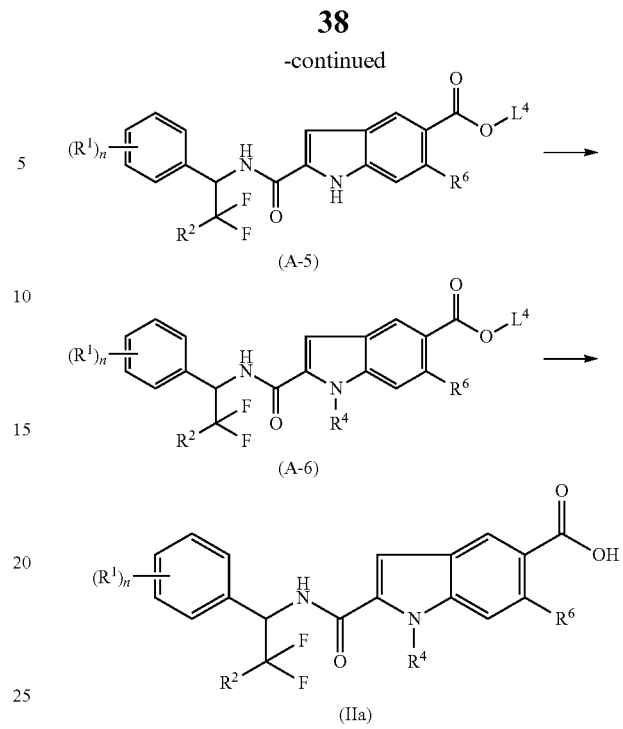
Benzimidazolecarboxylic acids of the formula (IIb) are novel and can be obtained, for example, according to Scheme 2.
Scheme 2
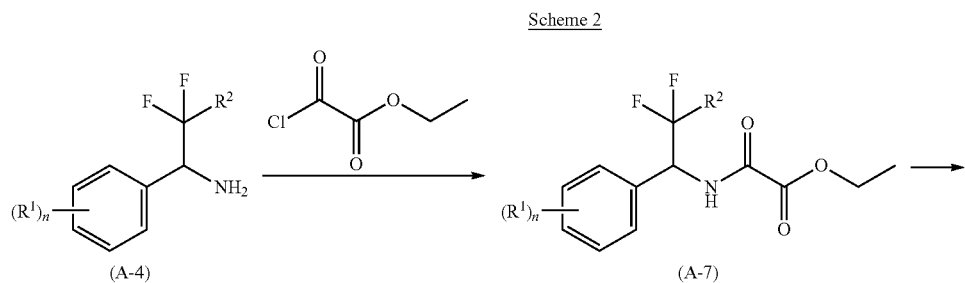
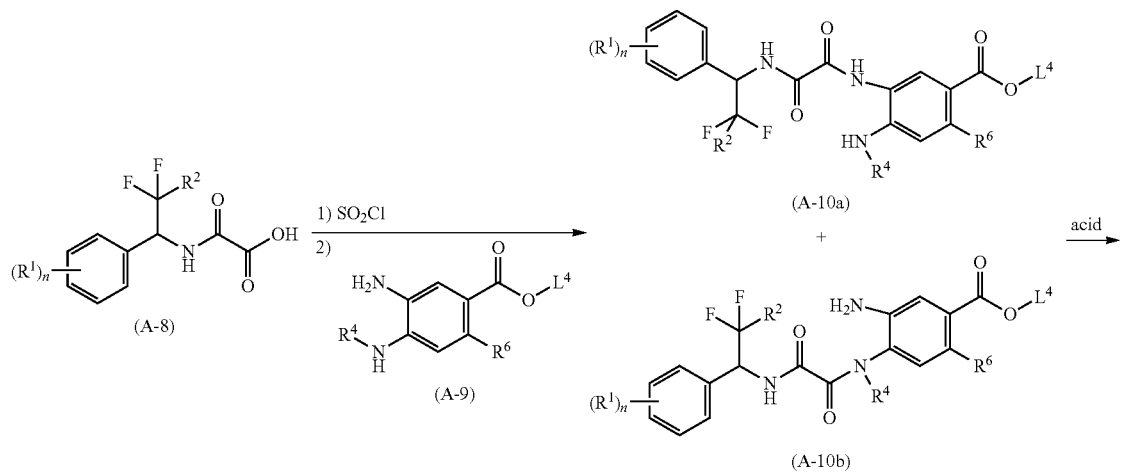

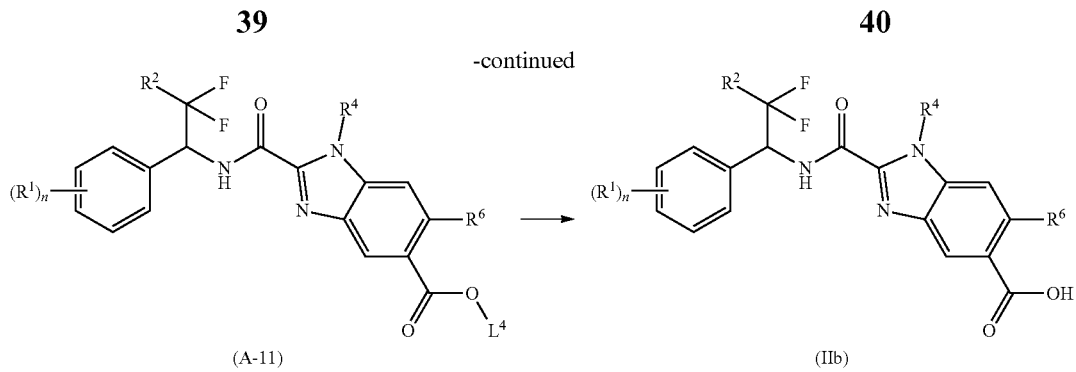

(A-11) (IIb)

Benzimidazole derivatives of the formula (IIb) are obtained from compounds of the formula (A-11) by hydrolysis using, for example, NaOH. Compounds of the formula (A-11) can be obtained from compounds of the formula (A-10b) by reaction in the presence of acidic catalysts such as, for example, 4-toluenesulphonic acid hydrate, hydrochloric acid or acetic acid. The reaction is carried out under the conditions disclosed in the literature for analogous compounds (cf., for example, EP1602648, Example 4; Journal of Medicinal Chemistry, 55 (2012) 9089-9106).

Compounds of the formula (A-10b) can be obtained together with compounds of the formula (A-10a) by initially reacting compounds of the formula (A-8) with thionyl chloride and then reacting the intermediate, which is not isolated, with 1,2-diaminophenyl derivatives of the formula (A-9). The reaction is carried out under the conditions disclosed in the literature for analogous compounds (cf., for example, EP1602648, Example 4; Journal of Medicinal Chemistry, 55 (2012) 9089-9106).

1,2-Diaminophenyl derivatives of the formula (A-9) are known (cf., for example WO2012/119984). Carboxylic acids of the formula (A-8) can be obtained by hydrolysis of esters of the formula (A-7).

Carboxylic acids of the formula (A-8) can be prepared analogously to processes known from the literature by ester hydrolysis from compounds of the general structure (A-7) (using, for example, NaOH or LiOH. For further methods see, for example, Tetrahedron 49 (1993) 3691-3748).

Compounds of the formula (A-7) are accessible by reacting amines of the formula (A-4) with ethyl 2-chloro-2-oxoacetate. The reaction is carried out under the conditions disclosed in the literature for analogous compounds (cf., for example, EP1997813, page 210, Example 8, Step 1).

Haloalkyl-substituted amines of the general formula (A-4) are commercially available, known from the literature or can be synthesized using processes known from the literature (cf., for example, WO2012/119984).

1-Aminocyclopropanecarbothioamide of the formula (VII) (CAS No. 1159877-97-0; WO2009/070485) is commercially available.

The processes according to the invention for preparation of the novel compounds of the formula (I) are preferably performed using a diluent. Useful diluents for performance of the processes according to the invention are, as well as water, all inert solvents. Examples which may be mentioned are: halohydrocarbons (e.g. chlorohydrocarbons such as tetrachlorethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, 1,4-dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene); nitriles (for example acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (e.g. pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl and isobutyl acetate, dimethyl, dibutyl and ethylene carbonate); amides (e.g. hexamethylphosphoramide, formamide, N-methylformamide, N,N-dimethylformamide, N,N-dipropylformamide, N,N-dibutylformamide, N-methyl-pyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (e.g. acetone, acetophenone, methyl ethyl ketone, methyl butyl ketone).

It is of course also possible to perform the process according to the invention in mixtures of the solvents and diluents mentioned.

When performing the process according to the invention, the reaction temperatures can be varied within a relatively wide range. In general, the process is carried out at temperatures between −30° C. and +150° C., preferably between −10° C. and +100° C.

The process according to the invention is generally performed under atmospheric pressure. However, it is also possible to perform the process according to the invention under elevated or reduced pressure generally at absolute pressures between 0.1 bar and 15 bar.

To perform the process according to the invention, the starting materials are generally used in approximately equimolar amounts. However, it is also possible to use one of the components in a relatively large excess. The reaction is generally performed in a suitable diluent in the presence of a reaction auxiliary, optionally also under a protective gas atmosphere (for example under nitrogen, argon or helium) and the reaction mixture is generally stirred at the temperature required for several hours. The workup is performed by customary methods (cf. the Preparation Examples).

The basic reaction auxiliaries used to perform the processes according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, 3-picoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine).

The acidic reaction auxiliaries used to perform the processes according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

The preparation and use examples which follow illustrate the invention without limiting it.

PREPARATION EXAMPLES

Synthesis Example 1

N5-(1-Carbamothioylcyclopropyl)-6-chloro-N2-[1-(3,5-dichloro-2,4-difluorophenyl)-2,2,2-trifluoroethyl]-1-ethylindole-2,5-dicarboxamide (Compound No. I-01)

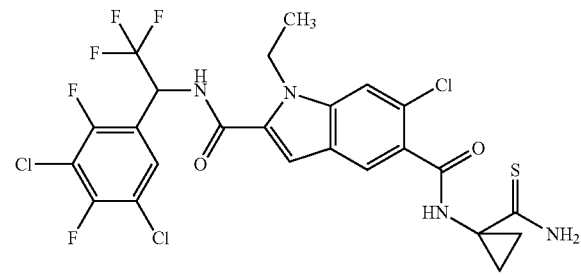 [SMILES: CCn1c(C(=O)NC(c2cc(Cl)c(F)c(Cl)c2F)C(F)(F)F)cc2cc(C(=O)NC3(C(N)=S)CC3)c(Cl)cc21]

6-Chloro-1-ethyl-2-({2,2,2-trifluoro-1-[3,5-dichloro-2,4-difluorophenyl]ethyl}carbamoyl)-1H-indole-5-carboxylic acid (prepared by the process according to WO-A-2012/119984, cf. page 64, line 16-page 65, line 1 and page 66, lines 8-11) (0.523 g, 0.98 mmol) was dissolved in DMF (9 ml). 1-Aminocyclopropanecarbothioamide (0.150 mg, 0.98 mmol), [benzotriazol-1-yloxy(dimethylamino)methylene] dimethylammonium hexafluorophosphate (0.374 g, 0.98 mmol) and N-methylmorpholine (0.200 g, 1.97 mmol) were added in succession, and the reaction mixture was then stirred at room temperature for 15 hours. Ethyl acetate was added, and the reaction mixture was washed successively with hydrochloric acid (1.0 M) and saturated sodium chloride solution and dried over magnesium sulphate, and the solvent was then distilled off under reduced pressure. The residue was chromatographed on silica gel using the mobile phase cyclohexane/ethyl acetate (60:40), which gave 0.430 g (67% of theory) of N5-(1-carbamothioylcyclopropyl)-6-chloro-N2-[1-(3,5-dichloro-2,4-difluorophenyl)-2,2,2-trifluoroethyl]-1-ethylindole-2,5-dicarboxamide. HPLC-MS: log P=4.25; mass (m/z): 627.0 (M+H)$^+$ Synthesis Example 2

The enantiomer separation of Synthesis Example 1 (Compound No. I-01) was carried out by preparative normal-phase chromatography on a chiral stationary phase using the following conditions: Column:

CHIRALPAK AS-H 5 μm–250×4.6 mm;

Mobile phase: A=n-heptane, B=methanol+ethanol (1:1), A:B=85:15; flow rate: 0.8 ml/min; 25° C.

430 mg of N5-(1-carbamothioylcyclopropyl)-6-chloro-N2-[1-(3,5-dichloro-2,4-difluorophenyl)-2,2,2-trifluoroethyl]-1-ethylindole-2,5-dicarboxamide (Synthesis Example 1, Compound No. I-01) gave:

171 mg of the compound I-18, (+)-enantiomer (retention time 7.5 minutes, ee>99%, optical rotation: +112.9°).

172 mg of the compound I-17, (−)-enantiomer (retention time: 9.8 minutes, ee>99%, optical rotation: −103.1°).

Synthesis Example 3

N5-(1-Carbamothioylcyclopropyl)-6-chloro-1-ethyl-N2-{2,2,2-trifluoro-1-[4-fluoro-3-(trifluoromethyl)phenyl]ethyl}-1H-benzimidazole-2,5-dicarboxamide (Compound No. I-30)

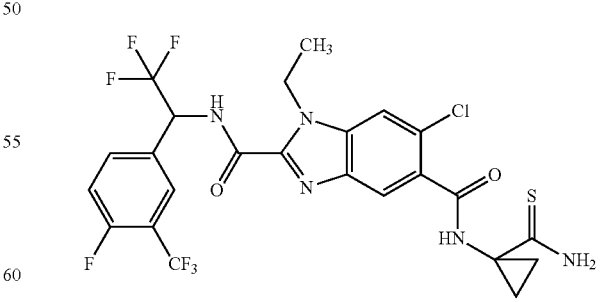

Step 1: Ethyl oxo({2,2,2-trifluoro-1-[4-fluoro-3-(trifluoromethyl)phenyl]ethyl}aminotacetate A mixture of 2,2,2-trifluoro-1-[4-fluoro-3-(trifluoromethyl)phenyl]ethanamine (15.0 g, 57.4 mmol) and 4-methylmorpholine (7.58 ml, 68.9 mmol) in trichloromethane (200 ml) was cooled to 0° C., a solution of ethyl oxalyl chloride (8.23 g, 60.3 mmol) in chloroform (100 ml) was slowly added dropwise and the mixture was then stirred with warming to room temperature for 15 hours. The reaction mixture was poured onto water and extracted twice with 5% strength sodium hydrogen phosphate solution, the organic phase was dried over sodium sulphate and the solvent was distilled off under reduced pressure. This gave 20.4 g (99% of theory) of ethyl oxo({2,2,2-trifluoro-1-[4-fluoro-3-(trifluoromethyl)phenyl]ethyl}amino)acetate which was processed further without any further purification. HPLC-MS: log P=3.17; mass (m/z): 362.0 $(M+H)^+$ Step 2: Oxo({2,2,2-trifluoro-1-1-[4-fluoro-3-(trifluoromethyl)phenyl]ethyl}aminotacetic acid Ethyl oxo({2,2,2-trifluoro-1-[4-fluoro-3-(trifluoromethyl)phenyl]ethyl}amino)acetate (20.42 g, 56.0 mmol) was initially charged in a mixture of methanol (200 ml) and water (26 ml), and sodium hydroxide (8.97 g, 224 mmol) was added with stirring. The reaction mixture was stirred at room temperature for 15 hours and most of the solvent was then distilled off under reduced pressure. The residue was taken up in water/tert-butyl methyl ether, the phases were separated and the aqueous phase was extracted twice with tert-butyl methyl ether. The aqueous phase was then acidified with 10% strength hydrochloric acid to pH 3 and extracted repeatedly with ethyl acetate. The combined organic phases were washed with saturated sodium chloride solution and dried over sodium sulphate, and the solvent was distilled off under reduced pressure. This gave 19.55 g (85% of theory) of oxo({2,2,2-trifluoro-1-[4-fluoro-3-(trifluoromethyl)phenyl]ethyl}amino)acetic acid which was processed further without any further purification. HPLC-MS: log P=1.84; mass (m/z): 332.0 $(M+H)^+$ Step 3a: Ethyl 5-amino-2-chloro-4-(ethylamino)benzoate Ethyl 2-chloro-4-(ethylamino)-5-nitrobenzoate: Ethyl 2-chloro-4-fluoro-5-nitrobenzoate (3.60g, 14.5 mmol) was initially charged in THF (28 ml), and a 2M solution of ethylamine in THF (14.5 ml, 29 mmol) was added. The mixture was then stirred at room temperature for 15 hours. For work-up, the reaction mixture was added to water and extracted twice with ethyl acetate. The combined organic phases were washed with water and 5% strength sodium hydrogen phosphate solution and dried over sodium sulphate, and the solvent was distilled off under reduced pressure. The residue was chromatographed on silica gel using cyclohexane/ethyl acetate, which gave 2.80 g (71.3% of theory) of ethyl 2-chloro-4-(ethylamino)-5-nitrobenzoate. HPLC-MS: log P=3.49; mass (m/z): 273.0 $(M+H)^+$ Ethyl 5-amino-2-chloro-4-(ethylamino)benzoate: Ethyl 2-chloro-4-(ethylamino)-5-nitrobenzoate (2.47 g, 9.05 mmol) was initially charged in ethanol (86 ml)/water (14 ml), and ammonium chloride (775.2 mg, 14.4 mmol) was added. The reaction mixture was warmed to 60° C., iron powder (5.06 g, 90.5 mmol) was added and the mixture was then stirred at reflux temperature for 3 hours. After cooling, the mixture was filtered through kieselguhr, the filter cake was washed repeatedly with ethanol and the solvent was distilled off under reduced pressure. The residue was taken up in ethyl acetate, the solution was washed with water and saturated sodium chloride solution and dried over sodium sulphate and the solvent was distilled off. This gave 2.16 g (83% of theory) of ethyl 5-amino-2-chloro-4-(ethylamino) benzoate. HPLC-MS: log P=2.31; mass (m/z): 243.0 $(M+H)^+$ Step 3: Ethyl 2-chloro-4-(ethylamino)-5-{[oxo({2,2,2-trifluoro-1-[4-fluoro-3-(trifluoromethyl)phenyl]ethyl}amino) acetyl]amino}benzoate Oxo({2,2,2-trifluoro-1-[4-fluoro-3-(trifluoromethyl)phenyl]ethyl}amino)acetic acid (2.30 g, 6.90 mmol) was dissolved in trichloromethane (50 ml), thionyl chloride (2.05 g, 17.2 mmol) and 2 drops of DMF were added and the mixture was stirred at 50° C. for 15 hours. The solvent was distilled off under reduced pressure and the residue was taken up in a little trichloromethane and added dropwise to a solution of ethyl 5-amino-2-chloro-4-(ethylamino)benzoate (2.16 g, 7.59 mmol) from Step 3a and triethylamine (2.4 ml, 17.2 mmol) in trichloromethane (25 ml). After 48 hours of stirring at room temperature, most of the solvent was distilled off under reduced pressure and the residue was taken up in water/ethyl acetate. The phases were separated and the aqueous phase was extracted twice with ethyl acetate. The combined organic phases were washed with 5% strength sodium hydrogen phosphate solution and dried over sodium sulphate, and the solvent was distilled off under reduced pressure. This gave 4.5 g (54% of theory) of ethyl 2-chloro-4-(ethylamino)-5-{[oxo({2,2,2-trifluoro-1-[4-fluoro-3-(trifluoromethyl)phenyl]ethyl}amino)acetyl]amino}benzoate which was reacted further without purification. HPLC-MS: log P=4.36; mass (m/z): 558.0 $(M+H)^+$ Step 4: Ethyl 6-chloro-1-ethyl-2-({2,2,2-trifluoro-1-[4-fluoro-3-(trifluoromethyl)phenyl]ethyl}carbamoyl)-1H-benzimidazole-5-carboxylate Ethyl 2-chloro-4-(ethylamino)-5-{[oxo({2,2,2-trifluoro-1-[4-fluoro-3-(trifluoromethyl)phenyl]ethyl}amino)acetyl] amino}benzoate (4.50 g, 8.06 mmol) was dissolved in toluene (90 ml), p-toluenesulphonic acid monohydrate (0.30 g, 1.61 mmol) was added and the mixture was stirred at reflux temperature on a water separator for 15 hours. After cooling, the mixture was washed with saturated sodium hydrogen carbonate solution and dried over sodium sulphate, and the solvent was distilled off under reduced pressure. The residue was chromatographed on silica gel using the mobile phase cyclohexane/ethyl acetate (80:20). This gave 0.99 g (20% of theory) of ethyl 6-chloro-1-ethyl-2-({2,2,2-trifluoro-1-[4-fluoro-3-(trifluoromethyl)phenyl] ethyl}carbamoyl)-1H-benzimidazole-5-carboxylate. HPLC-MS: log P=5.03; mass (m/z): 541.0 $(M+H)^+$ $^1$HNMR ($D_3$-DMSO): δ 1.33 (t, 3H), 1.37 (t, 3H), 4.37 (q, 2H), 4.60 (q, 2H), 6.36 (m, 1H), 7.64 (m, 1H), 7.69 (s, 1H), 8.21 (m, 2H), 8.42 (m, 1H), 8.62 (s, 1H).

Step 5: 6-Chloro-1-ethyl-2-({2,2,2-trifluoro-1-[4-fluoro-3-(trifluoromethyl)phenyl]ethyl}carbamoyl)-1H-benzimidazole-5-carboxylic acid Ethyl 6-chloro-1-ethyl-2-({2,2,2-trifluoro-1-[4-fluoro-3-(trifluoromethyl)phenyl]ethyl}carbamoyl)-1H-benzimidazole-5-carboxylate (0.495 g, 0.81 mmol) was initially charged in dioxane (25 ml)/water (2.8 ml), and lithium hydroxide (58.3 mg, 2.43 mmol) was added. The reaction mixture was stirred at room temperature for 48 h, after which the solvent was distilled off under reduced pressure. The residue was taken up in water and adjusted to pH 1 using concentrated hydrochloric acid. The precipitated solid was filtered off and dried. This gave 366 mg (83% of theory) of 6-chloro-1-ethyl-2-({2,2,2-trifluoro-1-[3-(trifluoromethyl) phenyl]ethyl}carbamoyl)-1H-indole-5-carboxylic acid.

HPLC-MS: log P=3.66; mass (m/z): 512.1 $(M+H)^+$ $_1$HNMR ($D_3$-DMSO): δ 1.31 (t, 3H), 4.60 (q, 2H), 6.30 (m, 1H), 7.64 (m, 1H), 8,06 (s, 1H), 8.2-8.3 (m, 3H), 8.43 (m, 1H).

Step 6: N5-(1-Carbamothioylcyclopropyl)-6-chloro-1-ethyl-N2-{2,2,2-trifluoro-1-[4-fluoro-3-(trifluoromethyl)phenyl]ethyl}-1H-benzimidazole-2,5-dicarboxamide (Compound No. I -30)

6-Chloro-1-ethyl-2-({2,2,2-trifluoro-1-[3-(trifluoromethyl)phenyl]ethyl}carbamoyl)-1H-indole-5-carboxylic acid (200 mg, 0.37 mmol) was dissolved in DMF (2 ml).

1-Aminocyclopropanecarbothioamide (62.2 mg, 0.40 mmol), [benzotriazol-1-yloxy(dimethylamino)methylene]dimethylammonium hexafluorophosphate (154 mg, 0.40 mmol) and N-methylmorpholine (112 mg, 1.11 mmol) were added in succession, and the mixture was then stirred at room temperature for 15 hours. The reaction mixture was poured onto water and extracted with ethyl acetate. After washing with saturated sodium chloride solution, the mixture was dried over magnesium sulphate and the solvent was then distilled off under reduced pressure. The residue was chromatographed on silica gel using the mobile phase cyclohexane/ethyl acetate (60:40), which gave 0.139 g (54% of theory) of N5-(1-carbamothioylcyclopropyl)-6-chloro-1-ethyl-N2-{2, 2, 2-trifluoro-1-[4-fluoro-3-(trifluoromethyl)phenyl]ethyl}-1H-benzimidazole-2,5-dicarboxamide.

HPLC-MS: log P=3.56; mass (m/z): 609.9 (M+H)$^+$.

The compounds of the formula (I) according to the invention described in Table 1 below are likewise preferred compounds according to the invention which are obtained according to or analogously to the Synthesis Examples described above.

TABLE 1

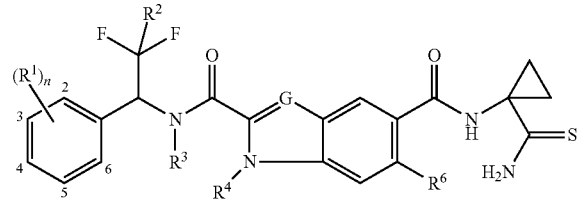

(I)

| No. | $(R^1)_n$ | $R^2$ | $R^3$ | $R^4$ | G | $R^6$ | $(M + H)^{+\ a)}$ | log p $^{a)}$ |
|---|---|---|---|---|---|---|---|---|
| I-01 | 2,4-F$_2$; 3,5-Cl$_2$ | F | H | Et | CH | Cl | 627.0 | 4.25 |
| I-02 | 3,5-Cl$_2$; 4-F | F | H | Et | CH | Cl | 610.0 | 4.04 |
| I-03 | 3-CF$_3$; 4-F | F | H | Et | CH | Cl | 609.1 | 3.70 |
| I-04 | 3-Cl; 4-F | F | H | Et | CH | Cl | 575.1 | 3.57 |
| I-05 | 3,4,5-Cl$_3$ | F | H | Et | CH | Cl | 625.0 | 4.33 |
| I-06 | 3-Br; 4-F | F | H | Et | CH | Cl | 619.0 | 3.64 |
| I-07 | 3-CF$_3$; 4-Cl | F | H | Et | CH | Cl | 625.1 | 3.96 |
| I-08 | 2,4-F$_2$; 3,5-Cl$_2$ | F | H | Me | CH | Cl | 613.0 | 3.94 |
| I-09 | 3,4-Cl$_2$; 5-F | F | H | Et | CH | Cl | 610.0 | 4.02 |
| I-10 | 3-F; 5-CF$_3$ | F | H | Et | CH | Cl | 609.0 | 3.81 |
| I-11 | 2-F; 3-Cl | F | H | Et | CH | Cl | 575.1 | 3.69 |
| I-12 | 2,4-F$_2$; 3,5-Cl$_2$ | F | H | prop-2-yn-1-yl | CH | Cl | 637.1 | 3.94 |
| I-13 | 3-CF$_3$; 4-Cl | F | H | Et | CH | Me | 605.0 | 3.89 |
| I-14 | 3,5-Cl$_2$; 4-F | F | H | prop-2-yn-1-yl | CH | Cl | 618.9 | 3.81 |
| I-15 | 3,5-Cl$_2$; 4-F | F | H | Me | CH | Cl | 595.0 | 3.76 |
| I-16 | 3-CF$_3$; 4-Cl | F | H | Me | CH | Cl | 611.1 | 3.70 |
| I-17 | 2,4-F$_2$; 3,5-Cl$_2$ | F | H | Et | CH | Cl | 627.0 | 4.27; (−)- enantiomer |
| I-18 | 2,4-F2; 3,5-Cl2 | F | H | Et | CH | Cl | 627.0 | 4.27; (+)- enantiomer |
| I-19 | 3-CF$_3$; 4-Cl | F | H | prop-2-yn-1-yl | CH | Cl | 635.1 | 3.73 |
| I-20 | 3,4,5-Cl$_3$ | F | H | Me | CH | Cl | 612.0 | 4.07 |
| I-21 | 3,4,5-Cl$_3$ | F | H | prop-2-yn-1-yl | CH | Cl | 636.0 | 4.09 |
| I-22 | 3-Cl; 5-CF$_3$ | F | H | Et | CH | Cl | 625.0 | 4.11 |
| I-23 | 3,5-F$_2$ | H | H | Et | CH | Cl | 541.0 | 3.07 |
| I-24 | 3,5-Cl$_2$ | F | H | Et | CH | Cl | 573.9 | 3.65 |
| I-25 | 3,4-Cl$_2$ | F | H | Et | CH | Cl | 573.9 | 3.54 |
| I-26 | 2,3,4-F$_3$; 5-Cl | F | H | Et | CH | Cl | 612.1 | 3.99 |
| I-27 | 2,5-F$_2$; 3,4-Cl$_2$ | F | H | Et | CH | Cl | 628.1 | 4.28 |
| I-28 | 2,4-F$_2$; 3,5-Cl$_2$ | H | H | Et | CH | Cl | 610.1 | 3.90 |
| I-29 | 2,3-F$_2$; 4,5-Cl$_2$ | F | H | Et | CH | Cl | 628.1 | 4.27 |
| I-30 | 3-CF$_3$; 4-F | F | H | Et | N | Cl | 609.9 | 3.46 |
| I-31 | 2,3,5-F$_3$; 4-Cl | F | H | Et | CH | Cl | 612.3 | 4.02 |
| I-32 | 3-CF$_3$; 4-F | H | H | Et | CH | Cl | 591.1 | 3.41 |

Abbreviations:
Et = ethyl,
Me = methyl;

a) The determination of the M$^+$ by LC-MS in the acidic range is effected at pH 2.7, acetonitrile (contains 0.1% formic acid) and water as eluents; linear gradient from 10% acetonitrile to 95% acetonitrile, instrument: Agilent 1100 LC system, Agilent MSD system, HTS PAL.

The log P values reported in the tables and Preparation Examples above were determined in accordance with EEC directive 79/831 Annex V.A8 by HPLC (High Performance Liquid Chromatography) using a reversed-phase column (C18). Temperature 43° C. The calibration is effected with unbranched alkan-2-ones (having 3 to 16 carbon atoms), for which the logP values are known.

b) The NMR data are determined with a Bruker Avance 400 equipped with a flow probe head (volume 60 μl), with tetramethylsilane as a reference (0.0) and the solvents $CD_3CN$, $CDCl_3$, $D_6$-DMSO.

The NMR data for selected examples are listed either in conventional form (δ values, multiplet splitting, number of hydrogen atoms) or as NMR peak lists.

NMR Peak List Method

The 1H NMR data of selected examples are stated in the form of 1H NMR peak lists. For each signal peak, first the δ value in ppm and then the signal intensity in round brackets are listed. The δ value signal intensity number pairs for different signal peaks are listed with separation from one another by semicolons.

The peak list for one example therefore takes the form of:

$\delta_1(\text{intensity}_1); \delta_2(\text{intensity}_2); \ldots ; \delta_i(\text{intensity}_i); \ldots ; \delta_n(\text{intensity}_n)$ The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of the $^1$H NMR spectra, use is made of tetramethylsilane and/or the chemical shift of the solvent, particularly in the case of spectra measured in DMSO. Therefore, the tetramethylsilane peak may, but need not, occur in NMR peak lists.

The lists of the $^1$H NMR peaks are similar to the conventional $^1$H NMR printouts and thus usually contain all peaks listed in a conventional NMR interpretation.

In addition, like conventional $^1$H NMR printouts, they may show solvent signals, signals of stereoisomers of the target compounds, which likewise form part of the subject matter of the invention, and/or peaks of impurities.

In the reporting of compound signals in the delta range of solvents and/or water, our lists of $^1$H NMR peaks show the usual solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional $^1$H NMR interpretation.

Further details of $^1$H NMR peak lists can be found in Research Disclosure Database Number 564025.

USE EXAMPLES

The examples which follow demonstrate the insecticidal and acaricidal action of the compounds according to the invention. In these examples, the compounds according to the invention cited relate to the compounds listed in Table 1 with the corresponding reference numerals (No.):

*Amblyomma Hebaraeum* Test

Solvent: dimethyl sulphoxide

To produce a suitable active compound formulation, 10 mg of active compound are mixed with 0.5 ml of dimethyl sulphoxide, and the concentrate is diluted with water to the desired concentration.

Tick nymphs (*Amblyomma hebraeum*) are placed into perforated plastic beakers and immersed in the desired concentration for one minute. The ticks are transferred on filter paper into a Petri dish and stored in a climate-controlled cabinet.

After 42 days, the kill in % is determined. 100% means that all of the ticks have been killed; 0% means that none of the ticks have been killed.

In this test, for example, the following compounds of the Preparation Examples show an efficacy of 100% at an application rate of 100 ppm: I-30.

*Boophilus microplus* Injection Test (BOOPMI inj)

Solvent: dimethyl sulphoxide

To produce a suitable active compound formulation, 10 mg of active compound are mixed with 0.5 ml of solvent and the concentrate is diluted with solvent to the desired concentration.

1 μl of the active compound solution is injected into the abdomen of 5 engorged adult female cattle ticks (*Boophilus microplus*). The animals are transferred into dishes and kept in a climate-controlled room.

The efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds of the Preparation Examples show an efficacy of 100% at an application rate of 20 μs/anim: I-01, I-02, I-03, I-04, I-05, I-07, I-08, I-09, I-10, I-11, I-12, I-13, I-16, I-17, I-18, I-19, I-20, I-22, I-23, I-24, I-25, I-26, I-27, I-29, I-30, I-31, I-32.

*Boophilus microplus*—Dip Test

Test animals: cattle ticks (*Boophilus microplus*) Parkhurst strain, SP-resistant Solvent: dimethyl sulphoxide 10 mg of active compound are dissolved in 0.5 ml of dimethyl sulphoxide. For the purpose of producing a suitable formulation, the active compound solution is diluted with water to the concentration desired in each case.

This active compound preparation is pipetted into tubes. 8-10 engorged adult female cattle ticks (*Boophilus microplus*) are transferred into a further tube with holes. The tube is immersed into the active compound formulation, and all the ticks are completely wetted. After the liquid has run out, the ticks are transferred on filter discs into plastic dishes and stored in a climate-controlled room.

The efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds of the Preparation Examples show an efficacy of 100% at an application rate of 20 ppm: 1-30.

*Ctenocephalides felis*—Oral Test (CTECFE)

Solvent: dimethyl sulphoxide

To produce a suitable active compound formulation, 10 mg of active compound are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be imbibed by the fleas through the parafilm membrane.

After 2 days, the kill in % is determined 100% means that all of the fleas have been killed; 0% means that none of the fleas have been killed.

In this test, for example, the following compounds of the Preparation Examples show an efficacy of 100% at an application rate of 100 ppm: I-01, I-02, I-03, I-04, I-05, I-07, I-08, I-09, I-10, I-11, I-12, I-13, I-16, I-17, I-18, I-19, I-20, I-22, I-23, I-24, I-25, I-26, I-27, I-29, I-30, I-31, I-32.

*Lucilia cuprina* Test (LUCICU)

Solvent: dimethyl sulphoxide

To produce a suitable active compound formulation, 10 mg of active compound are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the kill in % is determined 100% means that all the larvae have been killed; 0% means that none of the larvae have been killed.

In this test, for example, the following compounds of the Preparation Examples show an efficacy of 100% at an application rate of 100 ppm: I-01, I-02, I-03, I-04, I-05, I-07, I-08, I-09, I-10, I-12, I-13, I-16, I-18, I-19, I-20, I-22, I-24, I-25, I-26, I-27, I-29, I-30, I-31, I-32.

In this test, for example, the following compounds of the Preparation Examples show an efficacy of 90% at an application rate of 100 ppm: I-17, I-23.

*Musca domestica* Test (MUSCDO)

Solvent: dimethyl sulphoxide

To produce a suitable active compound formulation, 10 mg of active compound are mixed with 0.5 ml of dimethyl sulphoxide, and the concentrate is diluted with water to the desired concentration.

Vessels containing a sponge treated with sugar solution and the active compound preparation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds of the Preparation Examples show an efficacy of 100% at an application rate of 100 ppm: I-01, I-02, I-03, I-04, I-05, I-07, I-09, I-10, I-12, I-13, I-16, I-18, I-19, I-20, I-22, I-26, I-27, I-29, I-30, I-31.

In this test, for example, the following compounds of the Preparation Examples show an efficacy of 80% at an application rate of 100 ppm: I-17, I-24.

*Meloidogyne incognita* Test

Solvent: 125.0 parts by weight of acetone

To produce a suitable active compound formulation, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds of the Preparation Examples show an efficacy of 90% at an application rate of 20 ppm: I-19.

*Myzus persicae*—Spray Test

Solvent: 78 parts by weight of acetone 1.5 parts by weight of dimethylformamide

Emulsifier: alkylaryl polyglycol ether

To produce a suitable appropriate active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active compound formulation of the desired concentration.

After 6 days, the efficacy in % is determined. 100% means that all the aphids have been killed; 0% means that none of the aphids have been killed.

In this test, for example, the following compounds of the Preparation Examples show an efficacy of 100% at an application rate of 100 g/ha: I-29.

In this test, for example, the following compounds of the Preparation Examples show an efficacy of 90% at an application rate of 100 g/ha: I-20, I-32.

*Phaedon cochleariae*—Spray Test (PHAECO)

Solvent: 78.0 parts by weight of acetone 1.5 parts by weight of dimethylformamide Emulsifier: alkylaryl polyglycol ether To produce a suitable active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds of the Preparation Examples show an efficacy of 100% at an application rate of 100 g/ha: I-01, I-02, I-03, I-04, I-05, I-06, I-07, I-08, I-09, I-10, I-11, I-12, I-13, I-14, I-16, I-17, I-18, I-19, I-20, I-21, I-22, I-23, I-24, I-25, I-26, I-27, I-28, I-29, I-30, I-31, I-32.

In this test, for example, the following compound of the Preparation Examples show an efficacy of 100% at an application rate of 20 g/ha: I-15.

*Spodoptera frugiperda*—Spray Test (SPODFR)

Solvent: 78.0 parts by weight of acetone 1.5 parts by weight of dimethylformamide Emulsifier: alkylaryl polyglycol ether To produce a suitable active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active compound formulation of the desired concentration and, after drying, populated with caterpillars of the armyworm (*Spodoptera frugiperda*).

After 7 days, the efficacy in % is determined 100% means that all the caterpillars have been killed; 0% means that no caterpillars have been killed.

In this test, for example, the following compounds of the Preparation Examples show an efficacy of 100% at an application rate of 100 g/ha: I-01, I-02, I-03, I-04, I-05, I-06, I-07, I-08, I-09, I-10, I-11, I-12, I-13, I-14, I-15, I-16, I-17, I-18, I-19, I-20, I-21, I-22, I-24, I-25, I-26, I-27, I-28, I-29, I-30, I-31, I-32.

In this test, for example, the following compounds of the Preparation Examples show an efficacy of 83% at an application rate of 100 g/ha: I-23.

*Tetranychus urticae*—Spray Test, OP-Resistant (TETRUR)
Solvent: 78.0 parts by weight of acetone
1.5 parts by weight of dimethylformamide
Emulsifier: alkylaryl polyglycol ether To produce a suitable active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested by all stages of the greenhouse red spider mite (*Tetranychus urticae*) are sprayed with an active compound formulation of the desired concentration.

After 6 days, the efficacy in % is determined 100% means that all the spider mites have been killed; 0% means that none of the spider mites have been killed.

In this test, for example, the following compounds of the Preparation Examples show an efficacy of 100% at an application rate of 100 g/ha: I-01, I-02, I-04, I-06, I-07, I-08, I-09, I-10, I-11, I-13, I-14, I-16, I-17, I-18, I-19, I-20, I-21, I-22, I-23, I-24, I-25, I-26, I-27, I-28, I-30, I-31, I-32.

In this test, for example, the following compounds of the Preparation Examples shows an efficacy of 90% at an application rate of 100 g/ha: I-03, I-05, I-15, I-29.

*Spodoptera frugiperda*—Spray Test (SPODFR)
Solvent: 78.0 parts by weight of acetone
1.5 parts by weight of dimethylformamide
Emulsifier: alkylaryl polyglycol ether To produce a suitable active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active compound formulation of the desired concentration and, after drying, populated with caterpillars of the armyworm (*Spodoptera frugiperda*).

After the desired period of time, the efficacy in % is determined. 100% means that all the caterpillars have been killed; 0% means that no caterpillars have been killed.

In this test, for example, the following compounds of the Preparation Examples show superior efficacy to the prior art: see Table 2.

*Frankliniella occidentalis*—Spray Test (FRANOC)
Solvent: 7 parts by weight of dimethylformamide
Emulsifier: alkylaryl polyglycol ether To produce a suitable active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Bush bean plants (*Phaseolus vulgaris*) are sprayed with an active compound preparation of the desired concentration. After drying, the treated plants are infected with a mixed thrips population (*Frankliniella occidentalis*).

After the desired period of time, the plant-protective efficacy in % is determined. 100% means that no damage is evident; 0% means that the damage to the treated plant corresponds to that of the untreated control.

In this test, for example, the following compounds of the Preparation Examples show superior efficacy to the prior art: see Table 2.

*Diabrotica balteata*—Drench Test (DIABBA)
Solvent: 7 parts by weight of dimethylformamide
Emulsifier: 2 parts by weight of alkylaryl polyglycol ether To produce a suitable active compound formulation, 1 part by weight of active compound is mixed with the specified amounts of solvent and emulsifier, and the concentrate is diluted with water to the desired concentration, it being necessary to include the volume of soil which is drenched in the calculation. It should be ensured that a concentration of 40 ppm of emulsifier in the soil is not exceeded. To produce further test concentrations, water is used for dilution.

In each case 5 maize corns (*Zea mays*) are sown into pots filled with earth, and the next day the pots are watered with the active compound preparation of the desired concentration. After one day, 25 L2 larvae of the banded cucumber beetle (Diabrotica balteata) are added.

After 8 days, the efficacy in % is determined 100% means that all 5 plants have germinated and grown; 0% means that none of the plants has emerged.

In this test, for example, the following compounds of the Preparation Examples show superior efficacy to the prior art: see Table 2.

*Tetranychus urticae*—Spray Test; OP-Resistant (TETRUR)
Solvent: 78.0 parts by weight of acetone
1.5 parts by weight of dimethylformamide
Emulsifier: alkylaryl polyglycol ether To produce a suitable active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested by all stages of the greenhouse red spider mite (*Tetranychus urticae*) are sprayed with an active compound formulation of the desired concentration.

After the desired period of time, the efficacy in % is determined 100% means that all the spider mites have been killed; 0% means that none of the spider mites have been killed.

In this test, for example, the following compounds of the Preparation Examples show superior efficacy to the prior art: see Table 2.

TABLE 2

| Substance | Animal species | Concentration | % efficacy dat [a] |
|---|---|---|---|
| 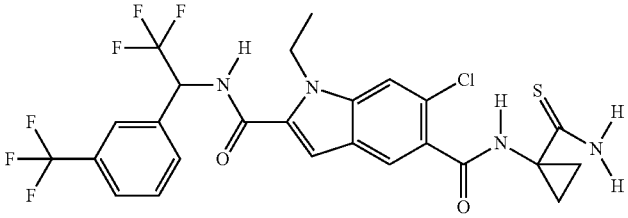<br>Prior art<br>Compound No. 273 WO-A-2012/119984 | SPODFR | 4 g/ha | 100 7 dat |
| | SPODFR | 0.8 g/ha | 33 7 dat |
| | FRANOC | 4 ppm | 98 7 dat |
| | FRANOC | 0.8 ppm | 60 7 dat |
| | DIABBA | 20 ppm | 60 8 dat |
| | DIABBA | 4 ppm | 70 8 dat |
| | TETRUR | 20 g/ha | 100 6 dat |
| | TETRUR | 4 g/ha | 70 6 dat |
| Ex. No. I-01 according to the invention | SPODFR | 4 g/ha | 100 7 dat |
| | SPODFR | 0.8 g/ha | 100 7 dat |
| Ex. No. I-02 according to the invention | SPODFR | 4 g/ha | 100 7 dat |
| | SPODFR | 0.8 g/ha | 100 7 dat |
| Ex. No. I-03 according to the invention | SPODFR | 4 g/ha | 100 7 dat |
| | SPODFR | 0.8 g/ha | 100 7 dat |
| Ex. No. I-04 according to the invention | SPODFR | 4 g/ha | 100 7 dat |
| | SPODFR | 0.8 g/ha | 100 7 dat |
| Ex. No. I-06 according to the invention | SPODFR | 4 g/ha | 100 7 dat |
| | SPODFR | 0.8 g/ha | 100 7 dat |
| Ex. No. I-07 according to the invention | SPODFR | 4 g/ha | 100 7 dat |
| | SPODFR | 0.8 g/ha | 67 7 dat |
| Ex. No. I-08 according to the invention | SPODFR | 4 g/ha | 100 7 dat |
| | SPODFR | 0.8 g/ha | 100 7 dat |
| Ex. No. I-10 according to the invention | SPODFR | 4 g/ha | 100 7 dat |
| | SPODFR | 0.8 g/ha | 100 7 dat |
| Ex. No. I-12 according to the invention | SPODFR | 4 g/ha | 100 7 dat |
| | SPODFR | 0.8 g/ha | 100 7 dat |
| Ex. No. I-15 according to the invention | SPODFR | 4 g/ha | 100 7 dat |
| | SPODFR | 0.8 g/ha | 83 7 dat |
| Ex. No. I-16 according to the invention | FRANOC | 4 ppm | 90 7 dat |
| | FRANOC | 0.8 ppm | 90 7 dat |
| | DIABBA | 20 ppm | 100 8 dat |
| | DIABBA | 4 ppm | 50 8 dat |
| Ex. No. I-18 according to the invention | SPODFR | 4 g/ha | 100 7 dat |
| | SPODFR | 0.8 g/ha | 100 7 dat |
| Ex. No. I-19 according to the invention | DIABBA | 20 ppm | 100 8 dat |
| Ex. No. I-20 according to the invention | SPODFR | 4 g/ha | 100 7 dat |
| | SPODFR | 0.8 g/ha | 100 7 dat |
| Ex. No. I-21 according to the invention | SPODFR | 4 g/ha | 100 7 dat |
| | SPODFR | 0.8 g/ha | 100 7 dat |
| Ex. No. I-22 according to the invention | SPODFR | 4 g/ha | 100 7 dat |
| | SPODFR | 0.8 g/ha | 100 7 dat |
| | TETRUR | 20 g/ha | 100 6 dat |
| | TETRUR | 4 g/ha | 100 6 dat |
| | DIABBA | 20 ppm | 100 8 dat |
| | DIABBA | 4 ppm | 50 8 dat |

[a] Abbreviations:
dat = days after treatment.

The table shows that the compounds according to the invention have superior biological efficacy to the compound No. 273 known from WO-A-2012/119984, in particular at low application concentrations.

This becomes evident in particular when Compound No. 273 of WO-A-2012/119984 is compared to the Compounds Nos. I-03 and I-07 according to the invention which differ from Compound No. 273 of WO-A-2012/119984 only in that the compounds according to the invention have an additional substitution by $R^1$=F (Compound No. I-03) or $R^1$=Cl (Compound No. I -07) in position 4 at the phenyl ring. Comparison of the biological activities shows the superiority of the group of compounds recently found.

This applies analogously to the comparison of Compound No. 273 of WO-A-2012/119984 and the Compounds Nos. I-10 and I-22 according to the invention which differ only in that the compounds according to the invention have, at the phenyl ring, a substitution by halogen in addition to a substitution by —$CF_3$.

This applies analogously to the comparison of Compound No. 273 of WO-A-2012/119984 and the Compounds Nos. I-16 and I-19 according to the invention which differ only in that the compounds according to the invention additionally have, at position 4 of the phenyl ring, a substitution by $R^1$=Cl and in which $R^4$ is not ethyl but methyl (Compound No. I-16) or prop-2-yn-1-yl (Compound No. I-19).

The invention claimed is:

1. A compound of formula (I)

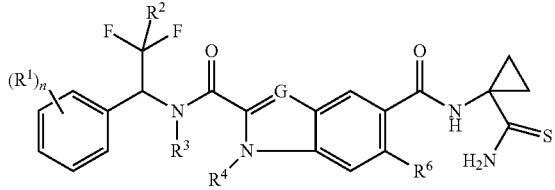

where
R¹ represents fluorine, chlorine, bromine, iodine, or trifluoromethyl
where at least one substituent R¹ represents fluorine, chlorine, bromine or iodine,
R² represents fluorine or hydrogen,
n represents 2, 3, or 4,
R³ represents hydrogen,
R⁴ represents hydrogen, methyl, ethyl, or prop-2-yn-1-yl,
G represents CH,
R⁶ represents chlorine, bromine, methyl, or trifluoromethyl,
and/or a salt and/or N-oxide of a compound of formula (I).

2. A compound according to claim 1 where
n represents 3 or 4,
and/or a salt and/or N-oxide of a compound of formula (I).

3. A compound of formula (I) according to claim 1 where
R¹ represents fluorine, chlorine, bromine or trifluoromethyl,
where at least one substituent R¹ represents fluorine or chlorine, and
n represents 2, 3 or 4,
and/or a salt and/or N-oxide of a compound of formula (I).

4. A compound of formula (I) according to claim 1 where R⁶ represents chlorine or methyl,
and/or a salt and/or N-oxide of a compound of formula (I).

5. An agrochemical formulation comprising a compound of formula (I) and/or a salt and/or N-oxide thereof according to claim 1 in a biologically effective amount of from 0.00000001 to 98% by weight based on the weight of the agrochemical formulation, and one or more extenders and/or surfactants.

6. An agrochemical formulation according to claim 5, additionally comprising a further agrochemically active compound.

7. A method for controlling animal pests which comprises allowing a compound of formula (I) and/or a salt and/or N-oxide thereof according to claim 1 to act on one or more animal pests and/or a habitat thereof, excluding methods for treatment of the human or animal body.

8. A method for protecting propagation material of one or more plants comprising employing a compound according to claim 1.

9. A compound of formula (I) according to claim 1, wherein R6 represents chlorine.

10. A compound of formula (I) according to claim 1 where R¹ represents fluorine, chlorine, or trifluoromethyl.

11. A compound of formula (I) according to claim 10, wherein n represents 2.

12. A compound of formula (I) according to claim 10, wherein n represents 3.

13. A compound of formula (I) according to claim 10, wherein n represents 4.

14. A compound of formula (I) according to claim 11, wherein R6 represents chlorine.

15. A compound of formula (I) according to claim 12, wherein R6 represents chlorine.

* * * * *